United States Patent [19]

Marsella et al.

[11] Patent Number: 4,558,157

[45] Date of Patent: Dec. 10, 1985

[54] SYNTHESIS OF DIMETHYLFORMAMIDE

[75] Inventors: John A. Marsella; Guido P. Pez, both of Allentown, Pa.

[73] Assignee: Air Products and Chemicals, Inc., Allentown, Pa.

[21] Appl. No.: 617,305

[22] Filed: Jun. 5, 1984

[51] Int. Cl.[4] .......................................... C07C 102/00
[52] U.S. Cl. ..................................... 564/132; 564/215
[58] Field of Search ................................ 564/132, 215

[56] References Cited

U.S. PATENT DOCUMENTS

| | | | |
|---|---|---|---|
| 3,099,689 | 7/1963 | Cragg | 260/561 |
| 3,412,151 | 11/1968 | Nozaki | 260/561 |
| 3,530,182 | 9/1970 | Haynes et al. | 260/561 |
| 4,218,398 | 8/1980 | Saito et al. | 260/561 |
| 4,224,243 | 9/1980 | Aoyama et al. | 260/561 |
| 4,230,636 | 10/1980 | Saito et al. | 260/561 |
| 4,244,889 | 1/1981 | Bartley et al. | 564/132 |
| 4,250,116 | 2/1981 | Bartley | 564/467 |
| 4,251,460 | 2/1981 | Fujita et al. | 564/132 |
| 4,269,998 | 5/1981 | Imai | 564/132 |
| 4,292,242 | 9/1981 | Laine | 260/326.8 |
| 4,302,598 | 11/1981 | Bellis | 564/132 |

FOREIGN PATENT DOCUMENTS 57-42660  3/1982  Japan .................................. 564/132

OTHER PUBLICATIONS

Kirk–Othmer, Encyclopedia of Chemical Technology, 3rd Edition (1980) vol. 11, pp. 264–265.

Primary Examiner—Anton H. Sutto
Assistant Examiner—John A. Sopp
Attorney, Agent, or Firm—Richard A. Dannells, Jr.; James C. Simmons; E. Eugene Innis

[57] ABSTRACT

In the catalytic reaction of ammonia or formamide with CO and $H_2$, exceptionally high yields of mono- and di-methyl formamide are obtained among the reaction products when the reaction is carried out in the presence of a platinum group catalyst soluble in the reaction medium, particularly a compound or complex of ruthenium or rhodium, employing a relatively non-volatile polar solvent which does not contain an active methyl function and which does not enter into the reaction producing formamide compounds. The pressure employed is in the range of 3000–8000 psi with a hydrogen partial pressure of at least 1500 psi, the preferred solvent being sulfolane.

14 Claims, No Drawings

SYNTHESIS OF DIMETHYLFORMAMIDE

FIELD OF THE INVENTION

This invention is concerned with the production of enhanced quantities of dimethylformamide in the reaction of ammonia with carbon monoxide and hydrogen.

BACKGROUND OF THE INVENTION

Dimethylformamide (DMF) is an important commercial commodity of extensive technical uses, particularly as a solvent for certain plastic coatings and films, a solvent for certain gases, dyes and electrolytes, a cleaner and paint remover, etc. The most commonly used processes for the production of DMF are (1) the one stage catalytic reaction of carbon monoxide and dimethylamine and (2) the two stage catalytic process wherein carbon monoxide is first reacted with methyl alcohol to produce methyl formate and the latter reacted with dimethylamine to obtain DMF.

As described by Kirk-Othmer: Encyclopedia of Chemical Technology 3rd edition (1980) vol. 11, pages 264–265, in the one stage process a solution of dimethylamine in methanol is reacted with carbon monoxide in the presence of catalyst such as sodium methylate or metal carbonyls, at 110°–150° C. and at pressure of 1.5–2.5 MPa (about 220–365 psi). In the two-stage process carbon monoxide and methanol are reacted in the presence of sodium methylate, at high pressure and at temperature of 60°–100° C., to obtain methyl formate which latter is recovered by distillation and then reacted with dimethylamine at 80°–100° C. and at low pressure.

Numerous other processes for the production of DMF are disclosed in prior patents. Typically among the more recent patents particularly concerned with the production of DMF, are the following:

U.S. Pat. No. 4,218,398 in which a mixture of alkylamines is reacted with carbon monoxide in the presence of a halogen-containing catalyst.

U.S. Pat. No. 4,224,243 in which a mixture of alkylamines, which may also contain monomethylformamide (MMF), is reacted with CO in the presence of hydrogen, over iron catalyst.

U.S. Pat. No. 4,230,636 wherein a mixture of alkylamines is reacted with carbon monoxide over iron catalyst.

U.S. Pat. No. 4,251,460 in which a mixture of di- and trimethylamines is reacted with CO. The said mixture of amines is obtained by reaction of methanol and ammonia in the presence of dehydration catalyst and removing resulting monomethylamine from the reaction mixture.

U.S. Pat. No. 4,269,998 in which a dialkylamine is reacted with $CO_2$ and water over copper chromite catalyst.

U.S. Pat. No. 4,302,598 wherein dimethylamine is reacted with CO in the presence of alkali metal methylate catalyst; excess of dimethylamine permits recycling and reuse of the catalyst.

Among earlier patents of interest, U.S. Pat. No. 3,412,151 discloses production of DMF by reaction of trimethylamine with water and $CO_2$ in the presence of dicobalt octacarbonyl catalyst at CO pressure in the range of 1000 to 6000 psig.

U.S. Pat. No. 4,244,889 is directed to the preparation of acetamides from CO, $H_2$ and a nitrogen-containing compound (ammonia or nitric oxide) over a solid catalyst comprising rhodium and manganese. Using ammonia as reactant and operating at a total pressure of 1000 psig, the obtained product is reported to contain principally about 31% methane, about 30% acetamides and about 14% acetic acid; among the remaining products there was included about 7.6% N,N-diethylformamide.

Other patents disclosing the use of rhodium and/or ruthenium catalyst in production of N-substituted formamides by reaction of an amine and an oxide of carbon include U.S. Pat. Nos. 3,099,689 and 3,530,182. U.S. Pat. No. 4,292,242 discloses the use of a mixed ruthenium carbonyl/iron carbonyl catalyst in aminomethylation by reaction of an olefin with an amine or ammonia in the presence of CO and hydrogen, wherein the catalyst is dissolved in a suitable solvent, among which are listed various alcohols, glycols, DMF, sulfolane, etc.

U.S. Pat. No. 4,250,116 is concerned with the production of methyl and ethyl amines by reaction of carbon monoxide and hydrogen with ammonia (or nitric acid) over heterogenous solid catalyst comprising rhodium and iron. The reaction product obtained is reported to contain about 38% of alkalamine, about 22% methane, about 27% alcohols and less than about 2% DMF; there is no report of the presence of MMF or unsubstituted formamide.

Published Japanese patent application Sho57-42660, is concerned with the manufacture of formamides by reaction of ammonia or an amine with carbon monoxide over rhodium oxide or other platinum group catalysts listed. With alkylamine as starting reactant the principal reaction product is the formamide corresponding to the particular alkylamine used.

SUMMARY OF THE INVENTION

It has now been found that relatively high quantities of mono- and di-methylformamides can be obtained along with unsubstituted formamide, by reaction of CO and ammonia or formamide in the presence of hydrogen at high $H_2$ partial pressure, employing platinum group catalyst and a non-volatile polar solvent which does not contain an active methyl function and which does not enter in the reaction to produce formamide compounds.

DETAILED DESCRIPTION

In accordance with the invention, when the reaction is carried out under the conditions hereinafter described, high yields of formamides are obtained in the reaction product from CO, $H_2$ and ammonium or formamide, including hitherto unexpected relatively large amounts of mono- and di-methylformamide. The necessary reaction conditions include elevated temperature, preferably in the range of 200°–235° C.; high total pressure in the range of 3000–8000 psi, preferably at about 5000 psi; high partial pressure of hydrogen, preferably at least 1500 psi; using a platinum group catalyst preferably a complex or compound of ruthenium or rhodium, said catalyst or reaction product thereof formed in the reaction medium, preferably being soluble in the solvent employed. The solvent employed for the reaction mixture is one that does not enter into the formamide producing reaction and is not consumed therein. The solvent must be of sufficient polarity and polarizability to stabilize the catalyst system, characterized by having a dielectric constant greater than 5 and preferably greater than 20 (as measured at 25° C. or the melting point of the solvent, whichever value is higher). Moreover, the solvent must not contain an active methyl function.

The molar ratio of $CO:H_2:NH_3$ or $CO:H_2$:formamide in the initial reaction mixture should comprise about 1:1:0.1 to about 1:1:2 and preferably about 1:1:0.2 to about 1:1:0.75.

The foregoing characterizations of the solvent excludes such solvents as methanol, methyl halides and methyl esters, which contain a reactive methyl group; and also excludes potentially reactive alcohols, halides and esters which might form undesired by-products because of reactive alkyl radicals therein. Also excluded are hydrocarbons and non-cyclics monoethers, because of their characteristically low dielectric constants.

A long but non-exhaustive list of suitable solvents can be found in Lange's Handbook of Chemistry (12th ed); McGraw-Hill, New York, 1979; Section 10, pp 103–116. Specific examples of suitable solvents include: sulfolane, 1-methyl-2-pyrrolidinone, dimethyl acetamide, 3-methyl solfolane, pyrrolidinone, tetrahydrofuran, 1,2-dimethoxyethane (glyme), diethylene glycol dimethyl ether (diglyme), triethylene glycol dimethyl (triglyme) and tetraethylene glycol dimethyl ether (tetraglyme). Ammonia or one of the reaction products of the $CO/H_2/NH_3$ reaction, could also be used as solvent for the stated reaction, such as formamide or mono- or di-methyl formamides.

The platinum group catalyst may be in the form of a complex or compound thereof, such as the carbonyl, oxide or hydrated oxide. The preferred catalyst is a compound or complex of ruthenium, particularly in the form of hydrated oxide or carbonyl, such as $RuO_2 \cdot x \cdot H_2O$ or $Ru_3(CO)_{12}$. Other platinum group catalysts which can be employed, but which were found to obtain lower yields of formamides, include $Rh_2O_3 \cdot 5H_2O$, $Rh_6(CO)_{16}$, $Os_3(CO)_{12}$, $IR_4(CO)_{12}$ and $Ir_2O_3 \cdot xH_2O$.

In the experimental runs in the examples hereinafter reported, a 175 cc Hasteloy C stainless steel autoclave reactor was employed equipped with a mechanical stirrer to aid intermixing of gases with the catalyst solution. The reactor was loaded with the solvent and the catalyst. It was then sealed, flushed with nitrogen and then with ammonia (with the exception of Example 6). After flushing specific amounts of ammonia were introduced (except in Example 6) by condensing in a known volume of liquid ammonia. The reactor was then attached to a high pressure line and charged with CO and $H_2$ to attain the desired initial pressure, after which the reactor was closed and heating commenced.

In most of the reactions hereinafter reported, a sharp pressure drop occurred within 30–40 minutes. The rate of heating was such that the reactor temperature was 200°–210° C. at this point. After the reactor had reached operating temperature and pressure had leveled off, the reactor was refilled with $CO/H_2$ to the desired reaction pressure. At the end of the reaction, the reactor was cooled, vented and opened. The liquids were collected and analyzed by gas chromatography.

A typical run made under preferred operating conditions is illustrated in Example 1 below:

EXAMPLE 1

The reactor was charged with 0.25 grams of $RuO_2 \cdot x \cdot H_2O$ (55% Ru) catalyst, 50 ml sulfolane and 3 grams $NH_3$. It was then pressurized to 3000 psi with a 1:1 $CO/H_2$ (molar) mixture. Heating was commenced and the pressure rose to about 3900 psi as the temperature increased. Upon attaining about 200° C., the pressure quickly dropped and stood at about 3200 psi when the temperature leveled off at 230° C. (1 hour total). The reactor was then repressured to 5000 psi with added $CO/H_2$ and heating was continued for an additional three hours (four hours total reaction time).

Analysis of the reaction products revealed the formation of 5.91 grams of total formamides (67% yield based on $NH_3$ feed), of which 70.7% was unsubstituted formamide, 16.1% MMF and 13.2% DMF.

EXAMPLE 2

A series of runs was carried out to determine the effect of varying selected parameters on formation of formamides from $CO/H_2/NH_3$ ($CO:H_2=1$ molar ratio). In all cases of this example 15 grams of ammonia were charged in 50 ml of sulfolane solvent; $Ru_3(CO)_{12}$ was employed as catalyst.

The results are reported in Table 1, below.

TABLE 1

| | Run No. | | | | | | |
|---|---|---|---|---|---|---|---|
| | 2(a) | 2(b) | 2(c) | 2(d) | 2(e) | 2(f) | 2(g) |
| Time (Hrs.) | 4 | 1 | 1 | 4 | 4 | 4 | 3.5 |
| $Ru_3(CO)_{12}$ (g) | 0.75 | 0.75 | 0.25 | 0 | 0.25 | 0.25 | 0.25 |
| Temp, (°C.) | 230 | 230 | 230 | 233 | 233 | 233 | 204 |
| Yields (g) | | | | | | | |
| Formamide | 2.60 | 6.09 | 7.68 | 0.30 | 5.21 | 6.28 | 9.24 |
| MMF | 0.93 | 0.83 | 0.49 | 0 | 0.57 | 0.74 | 0.52 |
| DMF | 0.67 | 0.27 | 0.08 | 0 | 0.16 | 0.23 | 0.10 |
| Init. Press. (25° C., psi) | 3000 | 3000 | 3000 | 3000 | 3000 | 4000 | 3000 |
| Refill Press. (psi) | 5500 | * | * | * | 5000 | 8000 | 5000 |

*No Refill

It was observed particularly from the runs reported in Table 1, that the following generalizations apply:

A. Lower temperatures and shorter reaction times lead to decreased yields of MMF and DMF and increased yields of unsubstituted formamide.
B. Higher catalyst concentrations give higher yields of MMF and DMF and lower yields of unsubstituted formamide.
C. Higher total pressures ($CO:H_2=1$) increase the yields of all amide products.

EXAMPLE 3

Another series of runs was carried out under conditions largely similar to those of Example 2, but with varying the quantity of $NH_3$ feed. In all these runs, 0.25 g $Ru_3(CO)_{12}$ was employed as catalyst in 50 ml of sulfolane solvent. The initial pressure was 3000 psi with 1:1 $CO/H_2$ at 25° C.; and the reactor was repressured to 5000 psi after the initial pressure drop ceased (about 1 hour). Temperature was in the range of 230°–234° C.

and the total reaction time 4 hours. The results are reported in Table 2, below.

TABLE 2

| | Run No. | | | | |
|---|---|---|---|---|---|
| | 2(e)* | 3b | 3c | 3d | 3e |
| $NH_3$ feed (g) | 15 | 9 | 6 | 3 | 1.5 |
| (moles) | (0.88) | (0.53) | (0.35) | (0.18) | (0.09) |
| Yields | | | | | |
| formamide (g) | 5.21 | 4.82 | 3.39 | 3.47 | 0.85 |
| (moles) | (0.116) | (0.107) | (0.075) | (0.077) | (0.019) |
| MMF (g) | 0.57 | 0.68 | 0.70 | 0.73 | 0.16 |
| (moles) | (0.010) | (0.012) | (0.012) | (0.012) | (0.003) |
| DMF (g) | 0.16 | 0.22 | 0.39 | 0.58 | 0.05 |
| (moles) | (0.002) | (0.003) | (0.005) | (0.008) | (0.001) |
| Total Moles formamides | 0.128 | 0.122 | 0.092 | 0.097 | 0.023 |
| Conversion % $NH_3$ to formamides | 15 | 23 | 26 | 54 | 26 |

*Run 2(e) is shown in the Table for comparison.

From the results reported in Table 2, it will be observed that absolute yields of both MMF and DMF increase with decreasing $NH_3$ feed. This increase holds until the amount of $NH_3$ fed falls below a molar ratio of about 1:1:0.3 $CO:H_2:NH_3$. Below this molar ratio reactor design may be the limiting factor, for most of the ammonia may be condensed in the unheated upper regions of the reactor. Formamide yields with $Ru_3(CO)_{12}$ show a drop with decreasing $NH_3$ feed, but with $RuO_2 \cdot H_2O$ as the ruthenium source (Table 3), formamide levels remain relatively constant. Qualitatively, however $RuO_2 \cdot xH_2O$ and $Ru_3(CO)_{12}$ have about the same activity for MMF and DMF formation. In both cases, a sharp drop in total production of formamides is seen at $NH_3$ feed levels less than 2 grams ($\approx 0.12$ mmols). Above about 10 grams ($\approx 0.6$ mmols $NH_3$) total percent conversion of ammonia to formamide compounds tends to drop off. The highest absolute conversion of $NH_3$ to DMF was found to take place when about 3 to 6 grams of $NH_3$ was used corresponding to molar ratio of $CO:H_2:NH_3$ of 1:1:0.3 to about 1:1:0.6.

EXAMPLE 4

Another series of runs was carried out under conditions of Example 3, but using instead of the ruthenium carbonyl catalysts, 0.25 grams of $RuO_2 \cdot xH_2O$ (55% Ru, $1.4 \times 10^{-3}$ mol Ru). The results are reported in Table 3 below.

stituted formamide accompanied by significant yields of mono- and di-methyl formamides. With the preferred ruthenium species catalyst and sulfolane as the reaction solvent, these reactions can be run up to 67% conversion (based on $NH_3$) by operating under ammonia lean conditions ($CO:H_2:NH_3 \approx 1:1:0.35$ molar ratio). In all cases the major product is formamide. Absolute yields of MMF and DMF increase significantly with lower levels of ammonia but yields of formamide are relatively invariant over a large range of ammonia feed levels.

In the foregoing description, the $RuO_2 \cdot xH_2O$ and $Ru_3(CO)_{12}$ were referred to as catalysts for the subject reaction, since these compounds were added to that reactor in that form. It is to be noted that these, as well as the other platinum group catalysts that can be employed, may not necessarily exert their catalytic activity in that form, but serve as percursors for the actual compound or complex catalyst formed in the reaction medium under operating conditions. The term "catalyst," as herein employed, will be understood to include the percursor as well as the active catalyst formed therefrom.

A series of tests were carried out to determine the effect of the nature of the solvent on the production of formamide by catalysts reaction of CO, $H_2$ and $NH_3$.

EXAMPLE 5

The reactions in this example were carried out except as otherwise noted, under conditions conforming to Example 2 of the cited Japanese publication Sho No. 57-42660. In each of the runs reported in Table 4 below,

TABLE 3

| | Run No. | | | | |
|---|---|---|---|---|---|
| | 4a | 4b | 4c | 4d* | 4e |
| $NH_3$ feed (g) | 15 | 9 | 6 | 3 | 1.5 |
| (moles) | (0.88) | (0.53) | (0.35) | (0.18) | (0.09) |
| Molar Ratio** $CO:H_2:NH_3$ | 1:1:1.75 | 1:1:1.05 | 1:1:.7 | 1:1:0.35 | 1:1:0.175 |
| Yields | | | | | |
| formamide (g) | 4.55 | 4.09 | 4.08 | 4.18 | 1.50 |
| (moles) | (0.101) | (0.091) | (0.091) | (0.093) | (0.033) |
| MMF (g) | 0.67 | 0.82 | 0.93 | 0.95 | 0.29 |
| (moles) | (0.011) | (0.014) | (0.016) | (0.016) | (0.005) |
| DMF (g) | 0.20 | 0.42 | 0.58 | 0.78 | 0.24 |
| (moles) | (0.003) | (0.006) | (0.008) | (0.011) | (0.003) |
| Total Moles formamides | 0.115 | 0.111 | 0.115 | 0.120 | 0.041 |
| Conversion % $NH_3$ to formamides | 13 | 21 | 33 | 67 | 46 |

*Same run as Example 1.
**Calculated for initial charge at 3000 psig

From the foregoing examples it is evident that under the conditions of the present invention CO, $H_2$ and $NH_3$ react to form reaction products comprising unsub- 1.5–2.0 grams of NH$_3$ (88–118 mmol) were employed, with 1.4 mmol of the indicated catalyst and 40 ml of the reported solvent. The reaction was performed at 185° C. at 1500 psi CO/H$_2$ (1:1, at 25° C.) over a 6 hour period.

TABLE 4

| | Run No. | | | | |
|---|---|---|---|---|---|
| | 5(a)[1] | 5(b) | 5(c) | 5(d) | 5(e) |
| Solvent | methanol | methanol | sulfolane | sulfolane | sulfolane |
| Catalyst | Rh$_2$O$_3$.5H$_2$O | RuO$_2$.xH$_2$O | RuO$_2$.xH$_2$O | Ru$_3$(CO)$_{12}$ | Rh$_2$O$_3$.5H$_2$O |
| Yield | | | | | |
| formamide (g) | 0.62 | 4.2 | 3.5 | 3.8 | 0.11 |
| (mmol) | (14) | (89) | (78) | (84) | (2) |
| MMF (g) | 0.20 | 0.94 | 0.14 | 0.16 | 0.02 |
| (mmol) | (3) | (16) | (2) | (3) | (<0.5) |
| DMF (g) | 0.10 | 0.16 | 0.02 | 0.02 | 0.01 |
| (mmol) | (1) | (2) | (<0.5) | <(0.5) | <(0.5) |

Apparently, from the results reported in Table 4, the bulk of the alkyl formamides formed in runs 5(a) and 5(b) resulted from reaction of NH$_3$ with the methanol solvent.

EXAMPLE 6

The reactor was charged with 0.25 grams of RuO$_2$·xH$_2$O (55% Ru) catalyst, 50 ml sulfolane and 11.3 grams formamide. It was then pressurized to 3000 psi with a 1:1 CO/H$_2$ molar mixture. The reactor was heated to 232° C. and held at the temperature for 4 hours.

Analysis of the reaction products revealed the formation of 1.22 g of MMF and 0.86 g DMF. Formamide (5.54 grams) was also present in the reaction mixture.

Other runs were carried out to determine the effect of various additives on the reaction system. In contrast to previous observations in the literature that Lewis bases tend to accelerate CO conversion, in the reactions involving reaction of CO, H$_2$ and NH$_3$ to form formamides these additives were found to display relatively little effect.

The preferred catalyst for the process of the present invention is a complex or compound of the ruthenium species, particularly RuO$_2$·xH$_2$O and Ru$_3$(CO)$_{12}$. Another ruthenium species that has proven activity, but less effective than the preferred carbonyl and hydrated oxides, is Ru(acetyl acetonate)$_3$. Other suitable but less effective catalysts are: Rh$_2$O$_3$·5H$_2$O, Rh$_6$(CO)$_{16}$, Ir$_4$(CO)$_{12}$ and Os$_3$(CO)$_{12}$. Also suitable is RuCl$_3$·xH$_2$O, provided it has been previously treated with CO and H$_2$ under conditions where it is known to be converted to a ruthenium carbonyl; see Bruce, *Ruthenium Carbonyls and Related Compounds*, Comprehensive Organometallic Chemistry edited by Wilkinson, et al., Vol. 4 Chapter 32.2, pp. 661–664, specifically Table 2 on p. 664, Pergamon Press (1982).

The foregoing and other platinum group catalysts may be employed in the form of their halides, oxides, carbonyls or compounds containing mixtures of these ligands, such as [RuCl$_2$(CO)$_3$]$_2$, Ru(CO)$_3$[P(C$_6$H$_5$)$_3$]$_2$, H$_4$Ru$_4$(CO)$_{12}$, [RhCl(C$_2$H$_4$)$_2$]$_2$, [RhCl(CO)$_2$]$_2$, Rh(CO)$_2$(acac), Rh$_2$(O$_2$CCH$_3$)$_4$, Rh(acac)$_3$, Ir(CO)$_2$-(acac) or [IrCl(CO)$_3$]$_n$; (acac=acetyl acetonate).

The preferred temperature for the reaction is 200°–235° C., with the most preferred being in the upper region of this range, as above about 220° C. At temperatures below 200° C. improved conversion of ammonia to formamide might be obtained but with greatly reduced production of MMF and DMF. No accompanying advantage is seen for use of temperatures above 235° C., and such temperatures would greatly increase the operating pressure of the system.

The preferred pressure range is 3000–8000 psi. Lower pressures result in lower rates of formation of all products. Higher pressures increase product yields; however, such higher pressures require greater care in reactor design and handling. To obtain optimum yields of alkylated formamides, the hydrogen partial pressure during reaction should be at or above 1500 psi, preferably at least 2000 psi.

To increase the overall production of DMF in the process of the present invention, the initial reaction product formed, which will contain unsubstituted formamide as well as mono- and di- methyl formamides, may be subjected to vacuum distillation to obtain DMF as distillate, the residual MMF and unsubstituted formamide can be recycled for reaction with CO in the presence of NH$_3$ and H$_2$ to form further quantities of DMF.

What is claimed is:

1. A process for the synthesis of N-methyl and N,N-dimethyl formamide which comprises reacting carbon monoxide and hydrogen with ammonia or formamide at an elevated temperature in the range of 200°–235° C., a total pressure in the range of 3000–8000 psi and a partial pressure of hydrogen of at least 1500 psi in the presence of a platinum group catalyst and in the further presence of a nonreactive, polar solvent which does not contain an active methyl function and has a dielectric constant greater than 5, as measured at 25° C. or at the melting point of the solvent whichever value is higher.

2. The process as defined in claim 1 wherein a relatively non-volatile solvent is employed.

3. The process as defined in claim 2 wherein said solvent is sulfolane.

4. The process as defined in claim 1 wherein the solvent employed is one which does not react with ammonia or formamide, carbon monoxide and hydrogen to form alkyl formamides.

5. The process as defined in claim 1 wherein the solvent employed has a dielectric constant greater than 20.

6. The process as defined in claim 1 wherein the catalyst employed is selected from the group consisting of carbonyls, oxides and hydrated oxides of said platinum group metals.

7. The process as defined in claim 1 wherein the catalyst employed comprises essentially a compound or complex of ruthenium.

8. The process as defined in claim 7 wherein said compound is RuO$_2$·xH$_2$O.

9. The process as defined in claim 8 wherein the initial reaction mixture comprises a molar ratio of carbon monoxide, hydrogen and ammonia or formamide, of about 1:1:0.1 to about 1:1:2.

10. The process as defined in claim 1 wherein the initial reaction mixture comprises a molar ratio of carbon monoxide, hydrogen and ammonia or formamide of about 1:1:0.2 to about 1:1:0.75, such that more than 30% of the ammonia is converted to formamides.

11. The process as defined in claim 7 wherein the catalyst employed is $Ru_3(CO)_{12}$.

12. The process as defined in claim 10 wherein said total pressure is at about 5000 psi.

13. The process as defined in claim 12 wherein the reaction products are subjected to vacuum distillation and the distillate comprising formamide and N-methyl formamide is recycled to the reaction to form further quantities of N,N-dimethyl formamide.

14. The process as defined in claim 1 wherein the reaction products are subjected to vacuum distillation and the distillate comprising formamide and N-methyl formamide is recycled to the reaction to form further quantities of N,N-dimethyl formamide.

* * * * *